(12) United States Patent
Wimmer et al.

(10) Patent No.: US 8,749,791 B2
(45) Date of Patent: Jun. 10, 2014

(54) APPARATUS AND METHOD FOR MEASURING OPTICAL PROPERTIES OF TRANSPARENT MATERIALS

(75) Inventors: Severin Wimmer, Munich (DE); Peter Schwarz, Koenigsdorf (DE)

(73) Assignee: BYK-Gardner GmbH (DE)

( * ) Notice: Subject to any disclaimer, the term of this patent is extended or adjusted under 35 U.S.C. 154(b) by 0 days.

(21) Appl. No.: 13/571,210

(22) Filed: Aug. 9, 2012

(65) Prior Publication Data

US 2013/0050684 A1 Feb. 28, 2013

(30) Foreign Application Priority Data

Aug. 31, 2011 (DE) .......................... 10 2011 053 140

(51) Int. Cl.
*G01N 21/55* (2014.01)
*G01J 1/04* (2006.01)
(52) U.S. Cl.
CPC .............. *G01N 21/553* (2013.01); *G01N 21/55* (2013.01); *G01J 1/04* (2013.01)
USPC .......................................... 356/445; 356/236
(58) Field of Classification Search
CPC .......... G01N 21/553; G01N 21/55; G01J 1/04
USPC ................... 356/445–448, 239.1–239.3, 236
See application file for complete search history.

(56) References Cited

U.S. PATENT DOCUMENTS 5,098,187 A * 3/1992 Judge ............................. 356/325
5,760,890 A * 6/1998 Lex et al. ...................... 356/236

FOREIGN PATENT DOCUMENTS

DE              29511344           1/1997  ............. G01N 21/59

* cited by examiner

*Primary Examiner* — Michael P Stafira
(74) *Attorney, Agent, or Firm* — Hayes Soloway P.C.

(57) ABSTRACT

An apparatus for measuring optical properties of transparent materials with a first illumination device which illuminates the material to be investigated along a pre-set illumination path with a pre-set radiation, with a radiation recording space which records radiation passed on by the material to be investigated. The radiation recording space is arranged so that radiation emitted by the first illumination device first strikes the material and then at least for a time an inner wall of the radiation recording space. A radiation detector device is arranged to record radiation reflected and/or scattered essentially only from the inner wall. A second illumination device suitable for emitting modulated radiation also illuminates the inner wall.

22 Claims, 2 Drawing Sheets

APPARATUS AND METHOD FOR MEASURING OPTICAL PROPERTIES OF TRANSPARENT MATERIALS

BACKGROUND OF THE INVENTION

The present invention relates to an apparatus and a method for measuring parameters of a sample which is translucent at least in part.

Translucent products such as for example glass, transparent sheets and the like are used in many fields. In this case the optical properties play an important role, depending upon the field of application. In this way for example, a high degree of transmission is required of glass panels and sheets which are used for greenhouses. A sheet used for packaging, on the other hand, should allow the contents to be recognized as clearly as possible and with as little clouding as possible.

A merely subjective observation of the optical quality of the material, as is nowadays frequently undertaken both in development and, in particular, in production, has the major drawback that the observations cannot be quantified at all or can be quantified only with a rough gradation, so that a comparison of the results is possible to only a very limited degree.

Apparatus have therefore been used in research and development in order to measure for example the degree of transmission of transparent materials. These apparatus have the drawback, however, that they are very complicated and do not allow different optical parameters to be determined which are necessary in order to evaluate the optical quality of the products.

DE 295 11 344 U1 describes an apparatus of this type for measuring optical parameters of transparent materials. In this case an illumination device is provided which irradiates light onto the material to be investigated, as well as a sample-recording space provided after this sample and a plurality of detector devices which detect the light reflected into this space. This apparatus thus allows parameters to be determined in accordance with a specified standard, namely the so-called ASTM standard. This standard is a standard testing method of determining the transmission of transparent plastics materials (ASTM=American Society for Testing Materials). The subject matter of DE 295 11 344 U1 is hereby also made the subject matter of the present application by reference in its entirety.

As well as this standard method, however, there is also a further standard method according to the ISO. In the case of this standard method the intention is also to take into consideration errors which occur as a result of change in efficiency—caused by the samples—of the Ulbricht sphere (integrating sphere) used. In this case for example single-beam methods are used, in which the sample to be investigated is applied to two different outlets of the Ulbricht sphere. In addition, double-beam methods are known, in which two light bundles are used, one constituting the measurement bundle which passes through the sample, and a further bundle which does not pass through the sample but illuminates the inner wall of the Ulbricht sphere. The last-named method has the drawback, however, that the aforesaid light bundles should be precisely attuned to each other and, in addition, influences from the background illumination (for example illumination of the space) should also be taken into consideration.

The object of the present invention is therefore to provide an apparatus and a method which are capable of being used as desired for the two standards named.

SUMMARY OF THE INVENTION

An apparatus according to the invention for measuring optical properties of transparent materials has a first illumination device which illuminates the material to be investigated along a pre-set illumination path with a pre-set radiation. In addition, the apparatus has a radiation recording space which records radiation passed on by the material to be investigated, the radiation recording space being arranged in such a way that the radiation emitted by the first illumination device first strikes the material and then—at least for a time and/or at least in part—an inner wall of the radiation recording space.

In addition, the apparatus has a first radiation detector device, which is arranged in such a way that it records radiation reflected and/or scattered essentially only from the inner wall of the radiation recording space, and a second illumination device, which illuminates the inner wall of the radiation recording space.

According to the invention the second illumination device is suitable for emitting modulated radiation. It is advantageous for the first and the second illumination devices to irradiate the radiation at irradiation angles different at least in part (in particular into the radiation recording space).

The whole of the light transmitted by the sample or the transparent material respectively then advantageously passes into the sphere or the radiation recording space respectively and is preferably detected by a sensor in an integral manner in the space of the sphere. The figure resulting from this corresponds to the transmission of the sample.

In addition, the haze can be calculated with a further method. The haze corresponds to the amount of light which is scattered by the sample and is not transmitted in a straight line through the sample. During this measurement the part of the surface of the sphere which rests on the opposite side of the measurement opening is opened by a covering device and then advantageously acts as a light trap. As a result, it is made possible for light which passes through the sample in a non-scattered manner and in a straight line to be absorbed in the light trap. Only scattered light is collected in the sphere and is supplied to a sensor which can correspond to the transmission sensor. The resulting figure provides information on the haze value of the sample.

It is advantageous for the radiation to be reflected out of the sample into the radiation recording space and to be mixed. The first radiation detector device is advantageously situated in the radiation recording space or in the wall thereof or it has at least one optical connection to this radiation recording space and preferably measures the light energy in the radiation recording space. This measurement corresponds to a transmission measurement.

If an area sensor which comprises a plurality of segments which are designed for example in the form of a central circle and surrounding annular sensors is used in the place of the light trap, then a clarity value can be determined with this. The clarity value describes the small angle scattering, i.e. a test is carried out into the appearance of the local intensity distribution of the light beam which passes through the sample in a substantially straight line.

It is advantageous for a calibration method to be provided for the measurement of the transmission—the haze and the clarity—in order to achieve standardized figures.

It is therefore advantageous for the apparatus to have a second radiation detector device which is advantageously arranged along the illumination path after the material to be investigated, in such a way that it records radiation irradiated along the illumination path.

This second radiation detector device can have in this case a sensor, for example circular, which is suitable for spatially resolved measurement and the centre of which is situated on or substantially on the optical axis or the illumination path respectively. In addition, the radiation detector device can have further sensor elements which, in particular, are annular and which are arranged—advantageously in a concentric manner—around the aforesaid, in particular circular, sensor.

The measurements mentioned above can be carried out with the commercially available appliance, "haze-gard", of the firm BYK Gardner GmbH.

It is preferable for the first illumination device to be suitable for emitting modulated radiation. In this case "modulated radiation" is understood to be radiation, the intensity of which changes over the course of time. In a preferred method the light beam is switched on and off. This can be carried out electronically or by a mechanical shutter method for example.

The modulation of the light is advantageous in this case in order to detect the influence of the ambient light which passes through the sample into the sphere and thus falsifies the measurement figure, and thus in order to correct the measurement figure. In particular, the transmission figure is highly susceptible to extraneous light which is produced by the ambient light.

If the ambient light is blanked out by a screened sample chamber, a compensation of the ambient light and therefore a modulation method are not necessary. As a result, however, the handling of the samples is made very difficult, since it is only possible to measure samples which fit into the sample chamber in terms of their size. In addition, the measurement chamber must always be closed in a light-proof manner during the measurement.

If the measurements are carried out in accordance with the method described in the ISO, then it is necessary for a compensation of the sample to be carried out. The measurement sample which rests against the sphere port changes in fact the efficiency of the Ulbricht sphere and as a result, the measurement results.

This falsification of the measurement results can be compensated in accordance with ISO by the influence of the measurement sample upon the efficiency of the sphere being detected optically in a calibration method on an additional second compensation port, which is also present on the sphere, and being compensated by way of calculation. These compensation steps have to be carried out afresh for each sample material, and this is very complicated. The compensation calibration described above can be avoided by the efficiency of the sphere being jointly measured automatically during a measurement and the measurement value being corrected with this figure or a variable of the measurement value derived from it.

As described above, in particular for the automatic measurement of the efficiency of the sphere, a second light source is used which illuminates the inside of the sphere and determines the efficiency of the sphere when a sample is applied. The light is measured with a sensor which can also be the transmission sensor. The correction figure can be determined by comparison with the efficiency figure of the sphere which has been determined without a sample and which for example is saved in a fixed manner in the appliance.

According to the invention this second radiation source emits a modulated or pulsed radiation. As a result, it is made possible for ambient light which passes through the sample into the sphere and thus falsifies the measurement of the efficiency of the sphere, to be capable of being detected and eliminated by way of calculation. In the case of this method it is advantageous for the sample space not to have to be closed off in a light-proof manner during the measurement, and this considerably accelerates the measurement procedure.

It is advantageous for the apparatus to have a covering device which is movable with respect to the radiation space in order to cover the second detector device. It is advantageous for this covering device to be displaceable or movable with respect to the radiation recording space or a wall of the radiation recording space respectively. In this way, the second detector device can be selectively covered, so that no radiation originating from the first illumination device will strike it.

If the covering device covers the second radiation detector device, the face of the covering device facing towards the interior of the radiation recording space is advantageously a component part of the internal surface or the inner wall of the radiation recording space respectively.

In the case of an advantageous embodiment the covering device or the covering element respectively can be moved out of the optical axis, so as to release in an advantageous manner a light trap (situated along the optical axis, in particular behind the covering device) which absorbs the radiation not deflected by the sample and so only light which is scattered by the sample and which is measured by a radiation detector device is recorded in the radiation recording space. In this way, a haze measurement can be carried out.

In addition, the covering device can also advantageously be moved out of the optical axis, so that as a result the light can strike a sensor, advantageously measuring in a spatially resolved manner.

It is advantageous for the radiation recording space to have a first opening on which a sample holder for recording the material to be investigated is arranged. It is advantageous for the radiation recording space to have no further opening by way of which radiation or light respectively can enter the radiation recording space from the outside.

The second radiation detector device is advantageously arranged along an irradiation axis or optical axis respectively of the light emitted by the first illumination device.

The radiation recording space is, in particular, a so-called Ulbricht sphere, at the opening of which the sample to be investigated is arranged. The interior of this Ulbricht sphere has a reflecting and/or bright surface which is used for measurement. The displaceable covering device is likewise advantageously provided with the sphere coating and, in a particularly preferred manner, can also have a spherical curvature. It is advantageous for the second (clarity) detector device to be provided with an opening through which the aforesaid optical axis extends and through which the radiation or the light respectively enters, after it has passed through the sample. The dimensions of this opening are determined by the guidelines in the standards. The face of the sensor is segmented into areas and is therefore capable of measuring the intensity distribution of the light beam.

It is advantageous for an inner wall of the radiation recording space to be made spherical.

In the case of a further advantageous embodiment the second illumination device is capable of being switched on or off respectively, so that the apparatus is capable of measuring in accordance with different standards.

In the case of a further advantageous embodiment the first and/or the second of the two light sources is or are a light emitting diode or a combination of light emitting diodes. An LED is thus particularly suitable since it has a low current consumption and a long service life.

In the case of a further advantageous embodiment the two illumination devices or the light sources thereof respectively have similar or identical illumination characteristics respectively, and in particular a similar or substantially identical spectral pattern. In this way it is advantageous, if different light sources are used for the two illumination devices, for the same type of light source to be used.

In the case of a further advantageous embodiment the illumination with the first illumination device and the illumination with the second illumination device are coupled to each other. In this way it would be possible for the second illumination device to be connected to a light source in a light conducting manner by way of a light conductor. It is advantageous for this to be the light source which also supplies the first illumination device with light or radiation respectively.

In this way too, it can be made possible for essentially the same light to be used for the illumination both of the sample and of the interior of the radiation recording space or respectively for the illumination to be carried out with comparable illumination properties.

It would also be possible, however, for the second illumination device not to be coupled to the first illumination device. In this way, the second illumination device could have a separate illumination source and/or a separate modulator. In this case the second illumination device can be activated and modulated independently of the first illumination device or illumination source respectively. In general, however, it is advantageous for a modulator device to be provided for modulating the second illumination device. In addition, a (first) pulse generation device can be provided which converts the radiation issuing from a light source (which is associated with the first and/or the second illumination device) into pulsed radiation.

In the case of a further advantageous embodiment at least one of the illumination sources emits a luminous flux which is constant over time. In this case regulating devices can be provided which carry out this emission of a luminous flux which is constant over time.

It is advantageous for the apparatus and, in particular, at least one of the illumination devices to have a device for measuring the change in the illumination characteristics of at least one illumination source and preferably both the illumination sources.

In addition, it can be provided that a measurement figure issued by the apparatus is corrected with the measurement of the change in the illumination characteristics of the illumination sources (in particular with the aid of a processor device).

It is preferable for apparatus to be provided in order to keep the light intensity constant or in order to detect the change in the light intensity and to correct it by way of calculation. In this case the change in the light intensity can be measured for example by blanking out part of the light beam and by subsequent detection and, in this way, the result can subsequently be corrected. As an alternative, it is also possible to measure an electrical parameter of the LED, such as for example the forward voltage, by which a correction can also be subsequently carried out. These correction methods can be used not only with semiconductor radiators but also with thermal radiators.

It is advantageous for the apparatus to have a second pulse generation device, so that pulsed radiation can also be generated for the illumination with at least one and preferably with the second illumination device. It is advantageous for the first and the second pulse generation devices to be arranged in such a way that an illumination of the radiation recording space takes place with the first and the second illumination devices staggered in time at least for a time and preferably staggered in time completely. It is advantageous for the radiation recording space not to be illuminated at any time both by the first illumination device and by the second illumination device.

In the case of an advantageous embodiment the first illumination device is suitable for the emission of modulated radiation. A modulation device can thus be provided for example for modulating the light beams of the first illumination device. This modulation device is advantageously a so-called "chopper screen". In this way it is made possible for the illumination device not to have to be switched on and off, which would alter its constant operation, but for the emergent light to be blocked for a time with the aforesaid chopper screen. In addition, a chopper device can also be provided in order to modulate or to chop the light of the second illumination device directly entering the radiation recording space.

As mentioned above, the apparatus advantageously has a pulse generation device which converts the radiation issuing from the light source—in particular radiated continuously—into pulsed radiation.

It would also be possible, however, for a radiation diversion device, such as for example a folding mirror, to be used in order to achieve illumination with the first illumination device and illumination with the second illumination device in a selective manner. Instead of a folding mirror, however, it would also be possible for a so-called switchable mirror, which can alter its reflective properties by being charged with electrical voltages or currents, to be used here.

In the case of a further advantageous embodiment the second illumination device is arranged on an inner wall of the radiation recording space in such a way that no beams of the illumination device strike a sensor or the opening of the sphere before the at least first reflection.

The present invention further relates to a method of measuring optical properties of transparent materials, in which radiation is irradiated by means of a first illumination device along a pre-set illumination path onto a material to be investigated and the radiation passed on by the transparent material in reaction to the irradiated radiation arrives at least in part and/or for a time at the inner wall of a radiation recording space and radiation reflected and/or scattered essentially only from the inner wall of the radiation recording space is recorded by means of a first radiation detector device. In addition, the inner wall of the radiation recording space is illuminated by a second illumination device, in particular capable of being switched on.

According to the invention the second illumination device emits modulated radiation. In this case it is advantageous to arrange the material to be investigated in the radiation path of the first illumination device. The modulated radiation is in particular, as mentioned above, pulsed radiation.

In the case of a further advantageous method the two illumination devices are supplied by at least one common light source.

It is advantageous for a covering device arranged inside the radiation recording space to be moved at least for a time. In this case this covering device can cover for a time a (measurement) outlet situated on the optical axis.

In the case of a further advantageous method the radiation passing through the material along a pre-set illumination path (which in particular coincides with the optical axis) is detected at least for a time by means of a second radiation detector device.

In the case of a further advantageous embodiment the first illumination device and the second illumination device emit radiation in a manner staggered with respect to each other in time at least in part and preferably staggered with respect to each other in time completely. In this way, a measurement in accordance with a multiplicity of standards, in particular the ASTM and ISO standards mentioned, is possible.

BRIEF DESCRIPTION OF THE DRAWINGS

Further advantageous embodiments may be seen in the accompanying drawings. In the drawings

DETAILED DESCRIPTION OF THE INVENTION

Figure 1:
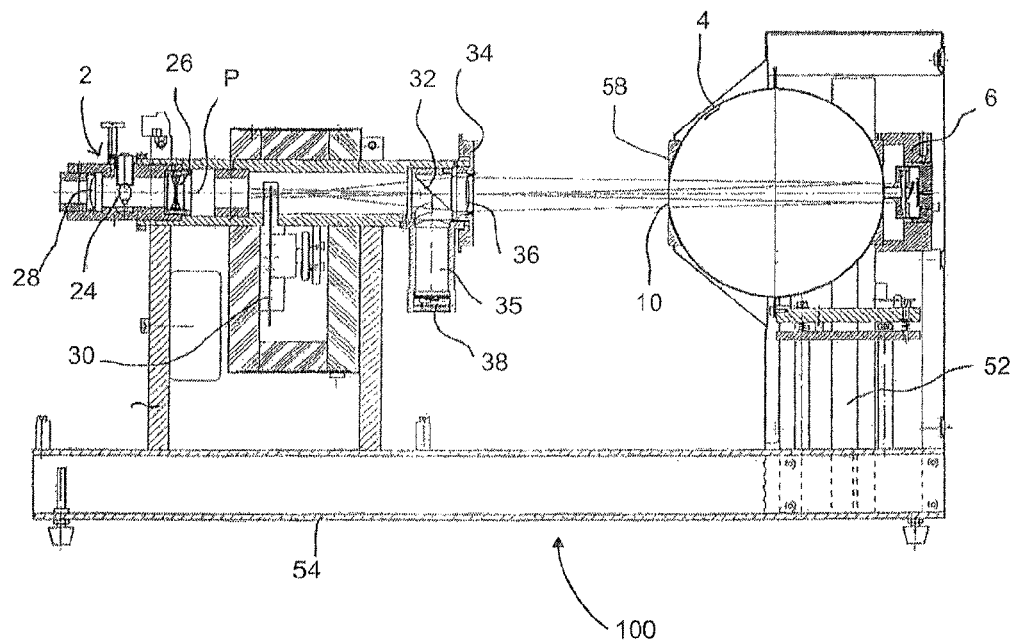
FIG. 1 shows an apparatus according to the prior art.

FIG. 1 shows an apparatus 100 according to the prior art for measuring optical properties of a transparent material 10. To this end an illumination device designated 2 in its entirety is provided which irradiates radiation onto the material 10 along an optical axis P. Expressed more precisely, a light source 24 is provided here, as well as a lens system with a lens 26 and a concave mirror 28, which bundle the light in a corresponding manner. The reference number 30 relates to a chopper screen which has the effect that the light is emitted from the first illumination device 2 in a modulated manner. Instead of this chopper screen, it would also be possible for example for an element such as a folding mirror to be used.

The reference number 32 designates a partially translucent mirror which directs a portion 35 of the radiation onto a detector device 38. A measure of the light intensity emitted is recorded with the aid of this detector device 38. In this way, the reference number 2 designates the first illumination device in its entirety and, in particular, also the optical design which performs the illumination of the material, as also referred to as the sample below.

The reference number 4 relates to a radiation recording space which in this case is designed in the form of an Ulbricht sphere and is arranged behind the material 10 in the direction of the optical axis P. The transmission and the haze can be determined with the aid of the shutter or the covering device 86. The reference number 6 relates to a second radiation detector device which is arranged along the optical path P and records the small angle scattering of the light passing through the material 10. The reference number 52 designates a carrier for the arrangement and the reference number 54 a main carrier.

Figure 2:
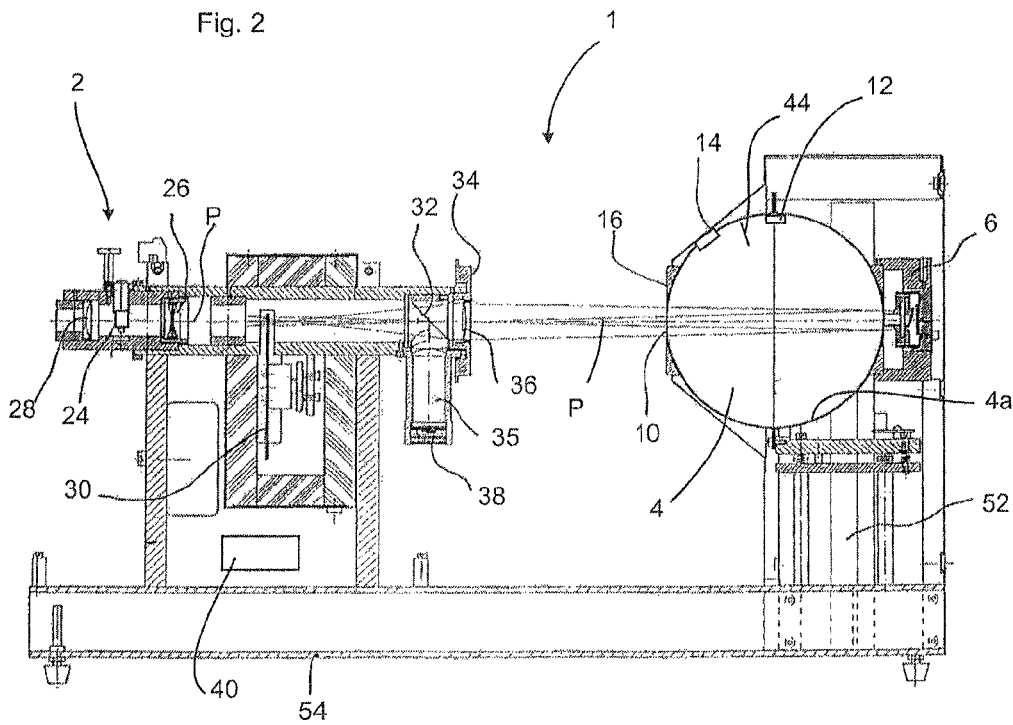
FIG. 2 shows an apparatus according to the invention.

FIG. 2 is an overall illustration of an apparatus 1 according to the invention. A crucial difference from the apparatus according to the prior art is a second illumination device 14 which is capable of being modulated and which is arranged in this case in an interior space of the radiation collecting space 4 and thus illuminates part of the inner wall 4a of the radiation recording space.

A light emitting diode 24 is provided here as a first illumination device. It is advantageous for this LED to emit white light, but it would also be possible for the LED to emit defined coloured light or to comprise for example a combination of LEDs of different spectral emission. In addition, it would be possible for filter elements, which allow the illumination of the sample 10 with light of different colour, to be arranged in the radiation path. Furthermore, optical elements such as diffusion discs, lenses or screens can be used in order to form or to homogenize the light beam in a suitable manner.

Figure 4:
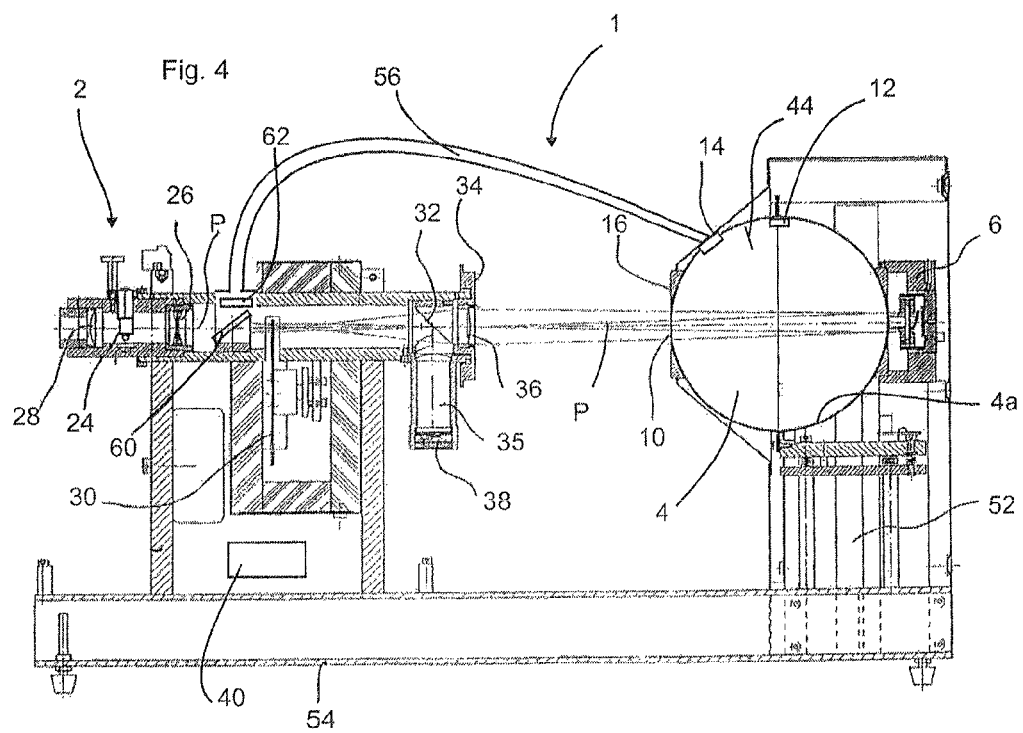
FIG. 4 shows a further embodiment of the present invention.

The illumination with the second illumination device can be decoupled from the first illumination in a suitable manner (cf. FIG. 4).

In the case of the design shown in FIG. 2 the second illumination device 14 has a separate light source which is capable of being controlled independently of the first light source 24. In this case the modulation would have to be carried out separately here. A chopper device (not shown) could thus be provided which would chop the light issuing from the second illumination device and entering the radiation recording space. In this way, it is possible for the second illumination device also to emit light with properties which are constant over time.

In this case the inner wall 4a is made radiation reflective, for example white or bright. In this way, the light is reflected a multiplicity of times at the inner wall 4a and so a uniform illumination can be achieved inside the radiation recording space, which can then be detected by the first radiation detector device 12. The blocking device 44 prevents radiation from being able to reach the first radiation detector device 12 directly. This blocking device 44 can be designed in this case in the form of a wall element which projects into the interior of the radiation recording space 4. In this case this wall element can be made radiation reflective itself, but it can also optionally be made radiation absorbent on the side facing towards the second illumination device 14.

The first radiation detector device 12 is used to record the light reflected and/or scattered at the inner wall 4a of the radiation recording space.

Figure 3:
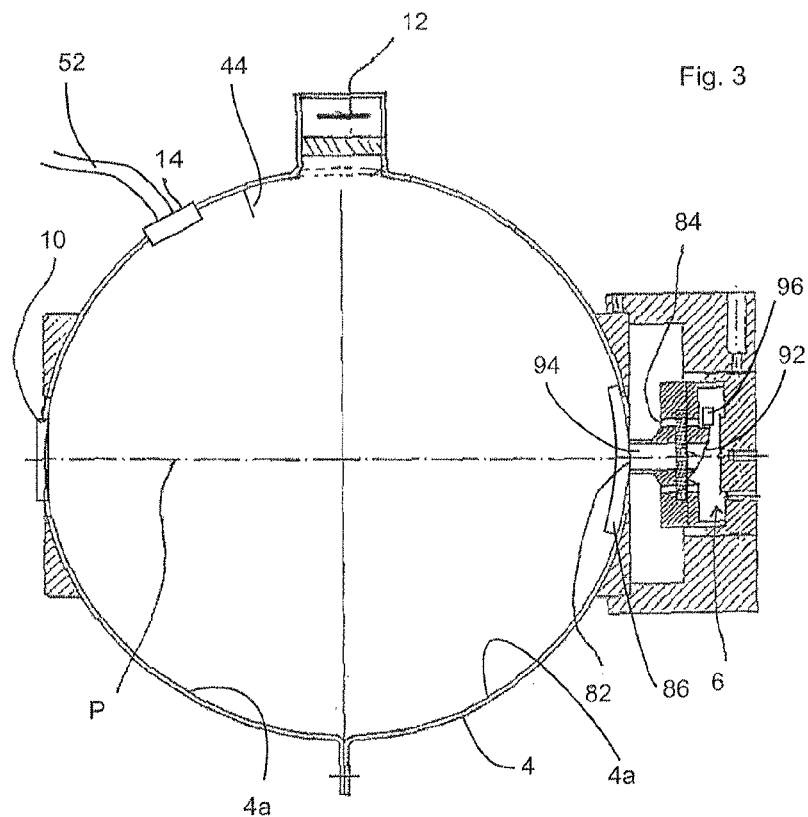
FIG. 3 is a larger illustration of the radiation recording space.

FIG. 3 is an enlarged illustration of the radiation recording space 4. The reference number 86 relates to a covering device which can free the opening 82. A measure of the quantity of light scattered in the sphere can be determined by the radiation detector device 12. Depending upon the setting of the covering element the transmission or haze figure can be calculated therefrom.

A second detector device 6 is illustrated in an optional manner. The reference number 92 relates to a first detector element which directly detects the radiation irradiated along the optical path P. In this case a channel 94 is provided which directly adjoins the inner wall 4a or an opening 82 situated in this inner wall. An inner wall of the channel 94 is made radiation absorbent for the irradiated light. In this way, it is possible for light irradiated essentially only along the optical axis P to reach the first detector element 92.

The reference number 84 designates a further channel which surrounds the channel 82 in an annular manner. Radiation can pass through this channel to a further detector element 96, the small angle scattering being detected in this way. The two detector elements 92, 96 are component parts of the second detector device 6 and thus allow the detection of that light which is irradiated along the optical axis and which is scattered at small angles with respect to the optical axis. The radiation detector device 6 is designed in such a way that it does not reflect any light back into the radiation recording space 4. When the covering device 86 is opened the sensor acts at the same time as a light trap.

In the case of the design shown in FIG. 3 the second illumination device 14 is arranged directly on the wall 4a of the radiation recording space 4. In this case the second radiation detector device is arranged above the radiation recording space.

It would also be possible, however, for the second illumination device 14 to project further into the radiation recording space 4. In addition, it would be possible for the second illumination device to be offset towards the outside with respect to the inner wall 4a of the radiation recording space. It would also be possible for a plurality of second illumination devices to be provided which illuminate the inner wall of the radiation recording space. In addition, the illumination device could be designed in such a way that the inner wall 4a of the radiation recording space is illuminated in part from the outside.

In addition, a further covering device could be provided, which can be pushed in front of the second illumination device 14, in which case a further covering device of this type is also advantageously made light-reflecting on the side facing the interior of the radiation recording space. It is advantageous for the first covering device 86 and, in a particularly preferred manner, also the further covering device to be displaceable or movable by means of elements formed outside the radiation recording space. It would also be possible, however, for motor drives for moving the covering devices to be provided.

The reference number 16 designates a sample holder by which the material to be investigated or the sample respectively is capable of being applied to the radiation recording space 4. In this case this sample holder is advantageously designed in such a way that no light can enter the radiation recording space 4 from the outside other than through the sample 10.

FIG. 4 shows a further design of an apparatus 1 according to the invention. In the case of the design shown here, in addition to the first modulation device 30 a second modulation device 62 is provided, which in this case however is shown only diagrammatically and which likewise has the effect that the light is passed on in a modulated manner to the light conductor 56. This second modulation device can likewise be a chopper screen and also, however, a further element which for example allows or prevents decoupling of light into the light conducting device 56.

It is advantageous for the two modulation devices to be arranged in such a way that the light issuing from the light source 24 passes only one of the two modulation devices 30, 62. It is preferable for a control device 40 to control the two modulation devices in a manner dependent upon each other, so that light is selectively emitted only along the optical path P or only by way of the second illumination device 14 or even, if desired, at the same time. In addition, it would be possible for only one modulation device to be provided, for example in the form of a folding mirror, which has the effect that light is irradiated into the radiation recording space 4 either only from the first illumination device 2 along the optical path P or only from the second illumination device 14.

It will be additionally seen that the region or the space respectively between the lens 36 and the material 10 is not covered, a corresponding referencing being achieved by the modulation of the light issuing in each case. The two modulation devices 30 and 62 are controlled in this case in such a way that the light of the illumination device 2 enters the radiation recording space 4 alternately along the path P and by way of the illumination device 14. The user of the apparatus 1 can thus choose whether he or she wishes to carry out the measurement in accordance with the ASTM standard or the ISO standard. If a measurement in accordance with the ASTM standard is desired, the measurement is not evaluated or carried out respectively with the second light source.

It is advantageous for the control device 40 to control the measurement sequence in such a way that it corresponds to the measurement standard fixed beforehand. It would also be possible, however, for the measurement to be carried out in the framework of measuring in accordance with the two standards and for the respective measurement results for the two measurement standards to be supplied to the user. For this purpose the apparatus can additionally have a display device (not shown) which emits the respective measurement results.

It would also be possible, however, for the radiation conducting device 56 used to be in the form of a system of mirrors or a light wave conductor which guides the light from the light source 2 to the radiation recording space 4 or into the interior thereof. In addition, it would also be possible for the radiation conducting device 56 to be guided inside the carrier. It would also be possible for the radiation conducting device 56 to be designed in such a way that a distance between the first illumination device and the radiation recording space 4 is altered in the direction of the optical axis P, without the radiation conducting device 56 having to be newly adjusted for this.

The Applicants reserve the right to claim all the features disclosed in the application documents as being essential to the invention, insofar as they are novel either individually or in combination as compared with the prior art.

LIST OF REFERENCES 1 apparatus
2 first illumination device
4 radiation recording space
4a inner wall of the radiation recording space
6 second radiation detector device
10 material, sample
12 first radiation detector device
14 second illumination device
16 sample holder
24 light source
26 lens
28 concave mirror
30 first modulation device
32 partially transparent mirror
35 portion
36 lens
38 detector device
40 control device
44 blocking element
52 carrier
54 main carrier
56 radiation conducting device, light conductor
60 radiation splitting device
62 second modulation device
82 opening
84 further channel
86 covering element
92 first detector element of the first radiation detector device 6 [sic]
94 channel
96 second detector element of the first radiation detector device 6 [sic]
100 apparatus (prior art)
P optical path, illumination path

The invention claimed is:

1. An apparatus for measuring optical properties of transparent materials with a first illumination device which illuminates the material to be investigated along a pre-set illumination path (P) with a pre-set radiation, with a radiation recording space which records radiation passed on by the material to be investigated, wherein the radiation recording space is arranged in such a way that the radiation emitted by the first illumination device first strikes the material and then at least for a time an inner wall of the radiation recording space, with a radiation detector device, which is arranged in such a way that it records radiation reflected and/or scattered essentially only from the inner wall of the radiation recording space, and with a second illumination device, which illuminates the inner wall of the radiation recording space, wherein the second illumination device is suitable for emitting modulated radiation, wherein the first and the second illumination devices irradiate the irradiation with angles different at least in art into the radiation recording space.

2. An apparatus according to claim 1, wherein the first illumination device is suitable for the emission of modulated radiation.

3. An apparatus according to claim 1, wherein the apparatus has a second radiation detector device which is arranged along the illumination path (P) after the material to be investigated, in such a way that it records radiation irradiated along the illumination path (P).

4. An apparatus according to claim 3, wherein the apparatus has a covering device which is movable with respect to the radiation recording space in order to cover the second radiation detector device.

5. An apparatus according to claim 1, wherein the two illumination devices have a similar or substantially identical spectral pattern.

6. An apparatus according to claim 1, wherein the illumination with the first illumination device and the illumination with the second illumination device are coupled to each other.

7. An apparatus according to claim 1, wherein the first illumination device and the second illumination device have a common light source.

8. An apparatus according to claim 1, wherein the second illumination device is connected to a light source in a light conducting manner by way of a light conductor.

9. An apparatus according to claim 1, wherein the apparatus has a first pulse generation device which converts the radiation issuing from the light source into pulsed radiation.

10. An apparatus according to claim 1, wherein the second illumination device is modulated with the aid of a modulator device.

11. An apparatus according to claim 1, wherein the second illumination device is not coupled to the first illumination device.

12. An apparatus according to claim 1, wherein the second illumination device has a separate illumination source and/or a separate modulator.

13. An apparatus according to claim 1, wherein at least one of the illumination sources emits a luminous flux which is constant over time.

14. An apparatus according to claim 1, wherein the apparatus and, in particular, at least one of the illumination devices have a device for measuring the change in the illumination characteristics of the illumination sources.

15. An apparatus according to claim 1, wherein at least one light source is a light emitting diode or a combination of light emitting diodes.

16. A method of measuring optical properties of transparent materials, wherein radiation is irradiated using a first illumination device along a pre-set illumination path (P) onto a material to be investigated and the radiation passed on by the transparent material in reaction to the irradiated radiation arrives at least in part and/or for a time at the inner wall of a radiation recording space and radiation reflected and/or scattered essentially only from the inner wall of the radiation recording space is recorded using a first radiation detector device, wherein the inner wall of the radiation recording space is illuminated by a second illumination device which is capable of being switched on, wherein the second illumination device emits modulated radiation, wherein the first and the second illumination devices irradiate the irradiation with angles different at least in art into the radiation recording space.

17. A method according to claim 16, wherein the first illumination device and the second illumination device emit radiation in a manner staggered with respect to each other in time at least in part.

18. The apparatus according to claim 1, wherein the second illumination device is arranged on an inner wall of the radiation recording space.

19. The apparatus according to claim 18, wherein the second illumination device is arranged in such a way, that no beams of the second illumination device strikes a sensor or an opening of the sphere before at least one reflection.

20. The apparatus according to claim 1, wherein the two illumination devices are supplied by at least one common light source.

21. The apparatus according to claim 1, wherein the second illumination device is arranged in an interior space of the radiation recording space.

22. The method according to claim 16, wherein the first illumination device and the second illumination device emit radiation in a manner staggered with respect to each other in time completely.

* * * * *

UNITED STATES PATENT AND TRADEMARK OFFICE
CERTIFICATE OF CORRECTION

PATENT NO. : 8,749,791 B2  
APPLICATION NO. : 13/571210  
DATED : June 10, 2014  
INVENTOR(S) : Wimmer et al.

Page 1 of 1

It is certified that error appears in the above-identified patent and that said Letters Patent is hereby corrected as shown below:

In the Claims

Claim 1, Col. 11, line 5, "art" should be --part--.

Claim 16, Col. 12, line 22, "art" should be --part--.

Signed and Sealed this
Thirtieth Day of September, 2014

Michelle K. Lee
*Deputy Director of the United States Patent and Trademark Office*